(12) United States Patent
Chen et al.

(10) Patent No.: US 8,196,596 B2
(45) Date of Patent: Jun. 12, 2012

(54) METHOD FOR TRACKING POLLUTION SOURCE IN PROCESS WATER

(75) Inventors: Chien-Hung Chen, Taoyuan County (TW); Ching-Yi Hsu, Kaohsiung (TW); Chen-Hua Chu, Taipei County (TW); Meng-Chun Huang, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/315,112

(22) Filed: Dec. 8, 2011

(65) Prior Publication Data
US 2012/0080387 A1    Apr. 5, 2012

Related U.S. Application Data

(62) Division of application No. 12/615,707, filed on Nov. 10, 2009, now Pat. No. 8,091,572.

(30) Foreign Application Priority Data

Nov. 11, 2008 (TW) .............................. 97143511 A (51) Int. Cl.
*E03B 1/00* (2006.01)

(52) U.S. Cl. .............. 137/2; 137/93; 210/96.1; 210/104; 210/143; 210/743; 210/744; 210/745; 210/746

(58) Field of Classification Search .................. None
See application file for complete search history.

(56) References Cited

U.S. PATENT DOCUMENTS

2004/0261844 A1 * 12/2004 Huang et al. .................. 137/93

* cited by examiner

*Primary Examiner* — Yelena G. Gakh
*Assistant Examiner* — Robert Xu
(74) *Attorney, Agent, or Firm* — Morris Manning & Martin LLP; Tim Tingkang Xia, Esq.

(57) ABSTRACT

A method for tracking a pollution source in process water is presented. Firstly, variation curves of drain water drained from different rinsing tanks are respectively obtained, and a water quality concentration of the drain water drained to a buffer tank is detected, so as to output a water quality variation curve. Then, an analytical comparison is performed on each drain water amount variation curve and the water quality variation curve within a same time interval, so as to output an analytical result of each flow of drain water in a range exceeding a predetermined water quality standard. In this manner, the drain water that exceeds the predetermined water quality standard can be tracked in real-time according to the analytical result, thereby quickly improving the process for discharging the drain water.

8 Claims, 8 Drawing Sheets

METHOD FOR TRACKING POLLUTION SOURCE IN PROCESS WATER

CROSS-REFERENCE TO RELATED APPLICATIONS

This application is a divisional patent application of, and claims benefit of U.S. patent application Ser. No. 12/615,707, filed Nov. 10, 2009, entitled "METHOD FOR TRACKING POLLUTION SOURCE IN PROCESS WATER", (hereinafter the "parent application",) filed in the name of Chien Hung Chen et al., which status is allowed. The parent application itself claims the benefit, pursuant to 35 U.S.C. §119(a) of Taiwanese Patent Application No. 097143511, filed Nov. 11, 2008. Each of the above applications is incorporated by reference herein in its entirety.

BACKGROUND OF THE INVENTION

1. Field of the Invention

The present invention relates to a tracking method, and more particularly to a method for tracking a pollution source in process water.

2. Related Art

Semiconductor, thin film transistor liquid crystal display (TFT-LCD), and other high-tech industries have become major industries in Taiwan. In the high-tech industries, after each process is completed, pure water or ultra-pure water is used for a great amount of rinsing steps, so as to ensure the stability of the next process, resulting in high water consumption in the high-tech industries. Secondly, since it is difficult to obtain water sources and develop water resources due to the special geographic environment of Taiwan, and the requirement for the reclaim rate of process water regulated in decrees becomes increasingly strict, it is one of important tasks in the high-tech industries of Taiwan to improve the reclaim rate of process water when water resources are limited, so as to reduce the waste of the water resources, thereby achieving water saving and environmental protection policy.

Moreover, if people attach importance to the improvement of the reclaim rate of the process water, but neglect the water quality of the reclaimed water, the application of the reclaimed water will be greatly limited, and even the quality of the ultra-pure water supply will be polluted, thereby reducing the production capacity. That is to say, the stability of the water quality of the reclaimed water has great effects. Therefore, it is a problem to be urgently overcome by persons skilled in the art to compromise the improvement of the reclaim rate of the process water and the water quality of the reclaimed water.

Rinsing water of a semiconductor wafer factory is taken as an example. Drain water from rinsing tanks for rinsing wafers is respectively drained through drains of the different tanks, gathered to a sub-main drain and a main drain in sequence, and then is drained to an intermediate tank (or called a buffer tank). In practice, the water quality (for example, conductivity, total organic carbon (TOC), pH value, and the like) of the drain water drained from each rinsing tank is not monitored during the draining process, but is monitored after the drain water is drained to the buffer tank. At this time, if the water quality of the rinsing drain water measured in the buffer tank satisfies an allowable standard value set by a reclaiming system, the rinsing drain water is drained to a process-water reclaiming system, that is, an ultra-pure water front end, for reclamation. However, once the water quality of the rinsing drain water measured in the buffer tank exceeds the allowable standard value set by the reclaiming system, in consideration of the yield, the water in the whole tank is guided to a waste water treatment system, and will not be reclaimed.

Briefly, when it is detected that the water in the buffer tank is seriously polluted, the water in the whole tank is directly drained to the waste water treatment system. As a result, a great amount of water is wasted. Moreover, since the drain water is drained to the buffer tank after being gathered through the drains of different sizes, and the water quality is monitored after the drain water is drained to the buffer tank, even if it is monitored that the water quality in the buffer tank exceeds the predetermined allowable standard value, it is impossible to know which rinsing tank the pollution source comes from. Therefore, it is a problem to be urgently overcome by persons skilled in the art to compromise the reclaim rate of the drain water and the stability of the water quality of the reclaimed water.

SUMMARY OF THE INVENTION

In view of the above problems, the present invention is a method for tracking a pollution source in process water, so as to compromise the reclaim rate of the drain water and the stability of the water quality of the reclaimed water, and to track the drain water that exceeds a predetermined water quality standard in real-time, thereby quickly improving the process for discharging the drain water.

The present invention provides a method for tracking a pollution source in process water, which comprises the following steps. Firstly, a plurality of flows of drain water is respectively drained to a buffer tank, and drain water amount variations of the flows of drain water drained from different draining tanks are synchronously detected, so as to respectively output a plurality of drain water amount variation curves corresponding to the flows of drain water. Next, a water quality concentration in the buffer tank is detected, so as to output a water quality variation curve. Then, an analytical comparison is performed on each drain water amount variation curve and the water quality variation curve within a same time interval, so as to respectively output an analytical result corresponding to each flow of drain water in a range exceeding a predetermined water quality standard.

The present invention provides a method for reclaiming process water, which comprises the following steps. Firstly, a plurality of flows of drain water is respectively drained from a plurality of rinsing tanks to a buffer tank, liquid level variations of the rinsing tanks are recorded, and a plurality of liquid level variation curves are respectively drawn. A water quality concentration in the buffer tank is synchronously detected, and a water quality variation curve is drawn. Next, each liquid level variation curve and the water quality variation curve within a same time interval are respectively superposed. Then, a peak overlap ratio of the water quality variation curve and the liquid variation curve after each superposition is respectively calculated in a range exceeding a predetermined water quality standard. Afterwards, the rinsing tank having a possible pollution source is determined according to the peak overlap ratio of each flow of drain water. Finally, a process for discharging the drain water at a front end of the process is adjusted and improved as soon as possible, that is, the flow of drain water of the rinsing tank having the possible pollution source is guided to a waste water tank, and the flows of drain water of other rinsing tanks are guided to a reclaiming tank, so as to facilitate subsequent reclamation.

Therefore, through the method of the present invention, the drain water that exceeds the predetermined water quality standard can be tracked in real-time, thereby quickly improving the process for discharging the drain water. In this manner, the water quality of the drain water in the buffer tank can be quickly stabilized, such that the flows of drain water are drained to the reclaiming system, that is, back to the ultra-pure water front end, and can be reused as ultra-pure water after simple water treatment.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
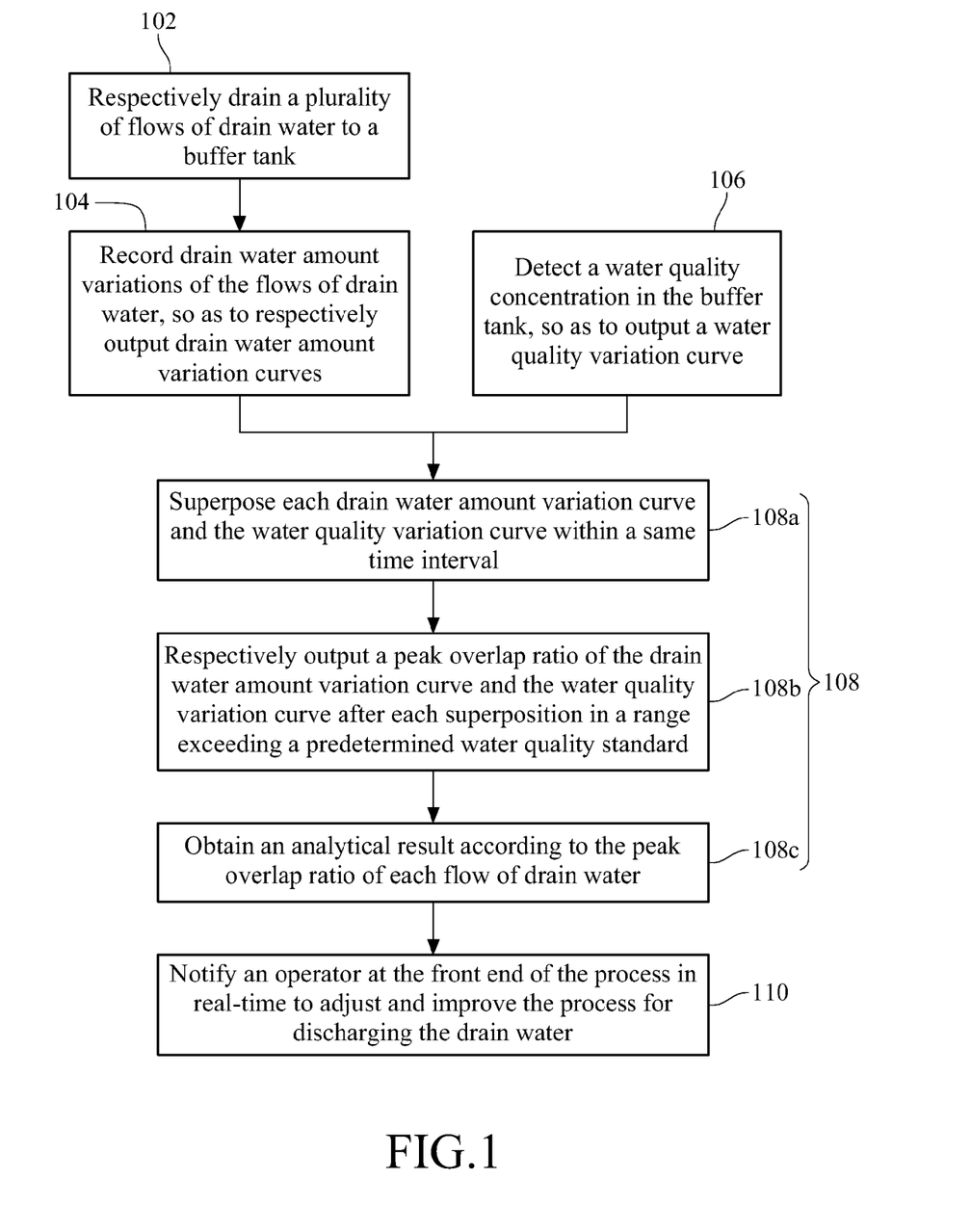
FIG. 1 is a schematic flow chart of a method for tracking a pollution source in process water according to an embodiment of the present invention.

FIG. 1 is a schematic flow chart of a method for tracking a pollution source in process water according to an embodiment of the present invention. Referring to FIG. 1, firstly, in Step 102, a plurality of flows of drain water is respectively drained from a plurality of rinsing tanks to a buffer tank. The buffer tank is connected to drain from the different rinsing tanks, and is a water tank disposed at a front end of the facility and used for analyzing the water quality of the drain water drained to the buffer tank. In Step 104, when the drain water is drained to the buffer tank, drain water amount variations of the flows of drain water drained from different draining tanks are respectively synchronously detected, so as to respectively output drain water amount variation curves corresponding to the flows of drain water. A water quality of at least one of the flows of drain water exceeds a water quality standard predetermined by a reclaiming system. In Step 106, a water quality concentration in the buffer tank is detected, so as to output a water quality variation curve.

Then, in Step 108, an analytical comparison is performed on each drain water amount variation curve and the water quality variation curve within a same time interval, so as to respectively output an analytical result corresponding to each flow of drain water in a range exceeding the predetermined water quality standard. Particularly, firstly, in Step 108a, each drain water amount variation curve and the water quality variation curve within the same time interval are respectively superposed, that is, a fingerprint recognized figure is formed. Afterwards, in Step 108b, in the range exceeding the predetermined water quality standard, a peak overlap ratio of the drain water amount variation curve and the water quality variation curve after each superposition is respectively output. Finally, in Step 108c, an analytical result is obtained according to the peak overlap ratio of each flow of drain water, that is to say, possibility that each flow of drain water has the pollution source can be known according to the peak overlap ratio. In this manner, with reference to the possibility, a user can quickly find out the rinsing tank most possibly having the pollution source, thereby adjusting the process for discharging the drain water as soon as possible.

Referring to FIG. 1, in Step 110, after the rinsing tank most possibly having the pollution source is found out, an operator at the front end of the process is notified in real-time to adjust and improve the process for discharging the drain water, for example, to control an electric valve for adjusting a flow direction of the drain water. In this manner, the water quality of the drain water in the buffer tank can be gradually stabilized, such that the flows of drain water are drained to the reclaiming system, that is, back to the ultra-pure water front end, and can be reused as ultra-pure water after simple water treatment.

FIGS. 2A-2F are liquid level variation curves obtained by respectively detecting liquid level variations in a first rinsing tank to a sixth rising tank according to an embodiment of the present invention. Referring to FIGS. 2A-2F, in this embodiment, six rinsing tanks (the first to the sixth rinsing tanks) and one buffer tank are used for explanation and description. Firstly, for example, through electronic signals of a pneumatic valve or the electric valve provided by a console, data captured by the console, or data detected by a water amount detector, liquid level variations in the first to the sixth rinsing tanks are respectively recorded, and then a plurality of liquid level variation curves corresponding to the liquid level variations of the first to the sixth rinsing tanks are respectively drawn, as shown in FIGS. 2A-2F. Here, the flows of drain water may be drained from the first to the sixth rinsing tanks at different time points. The method for recording the liquid level variations of the rinsing tanks is not intended to limit the scope of the present invention, and variations may be made to the present invention by persons of ordinary skill in the art.

Figure 3A:
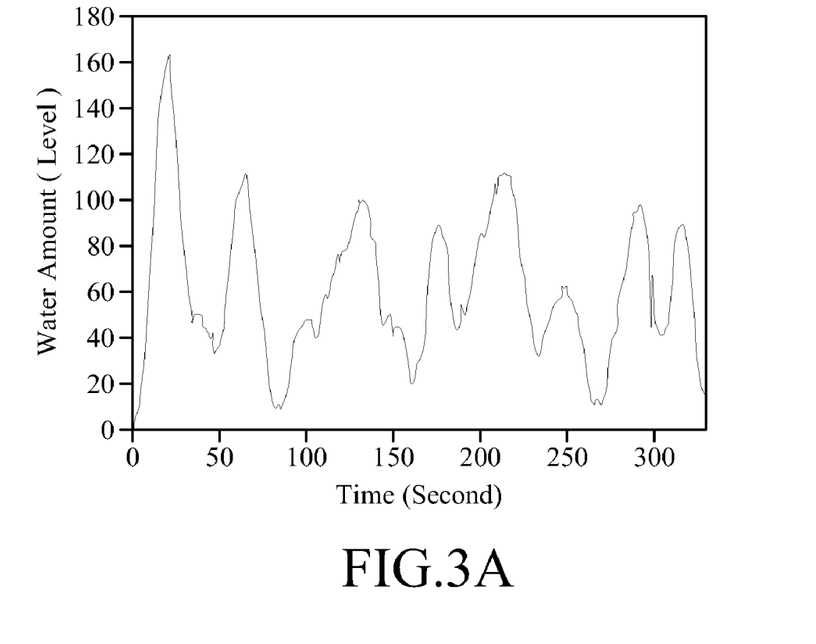
FIGS. 3A and 3B respectively show a liquid level variation and a water quality concentration of drain water in a buffer tank according to an embodiment of the present invention.
Figure 3B:
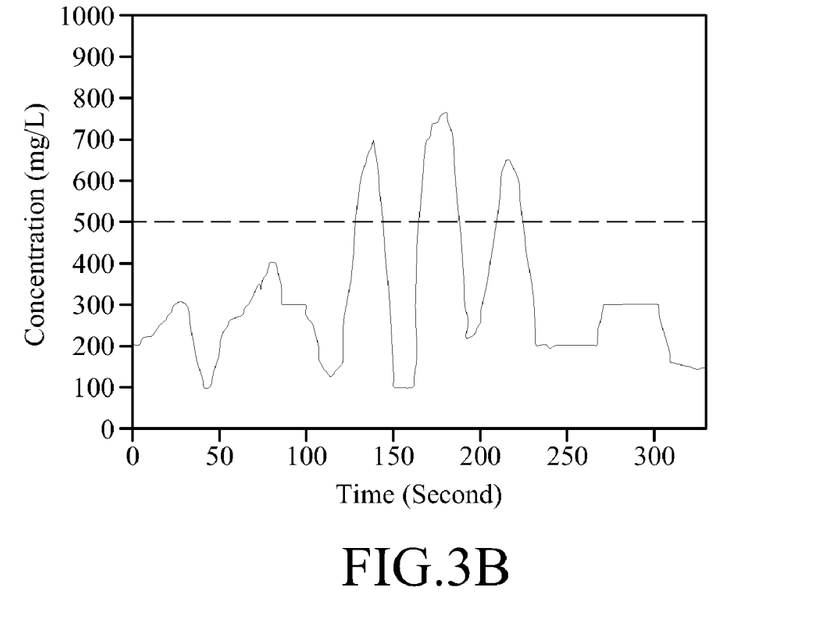

Next, when the liquid level variations of the first to the sixth rinsing tanks are recorded, a liquid level variation and a water quality concentration of the drain water in the buffer tank are detected, and a liquid level variation curve and a water quality variation curve are drawn, as shown in FIGS. 3A and 3B respectively. The water quality may be, for example, TOC, conductivity, pH value, fluoride ion, or the like. In this embodiment, the monitored water quality of the drain water is TOC. Moreover, each reclaiming system sets a water quality standard value, serving as a standard for determining whether to reclaim the drain water or not. In this embodiment, the set water quality standard is 500 mg/L, as shown by a dashed line of FIG. 3B.

It should be noted that, before the analytical comparison is performed, the drain water amount variation curves of the rinsing tanks or correct the water quality variation curve of the buffer tank must be selectively corrected based on a delay time of each flow of drain water. Therefore, all the curves shown in this embodiment have been corrected based on the delay time. Particularly, the delay time refers to a time difference between a time point at which a pollutant is detected in the rising tank and a time point at which the pollutant has been drained to the buffer tank. Secondly, the delay time is calculated by a delay time correction method, that is, calculated through a relation with a plurality of delay factors such as pipe length, pipe area, pipe curvature, pipe inclination, flow time, flow rate, and flow capacity, and through a predetermined correction method obtained according to requirements. In other words, the delay time can be calculated by using a formula depending on the delay factors and the predetermined correction method according to practical requirements such as pipe length, pipe area, pipe curvature, and other conditions. The delay time or the correction method is not intended to limit the scope of the present invention, and variations may be made to the present invention by persons of ordinary skill in the art.

Figure 2A:
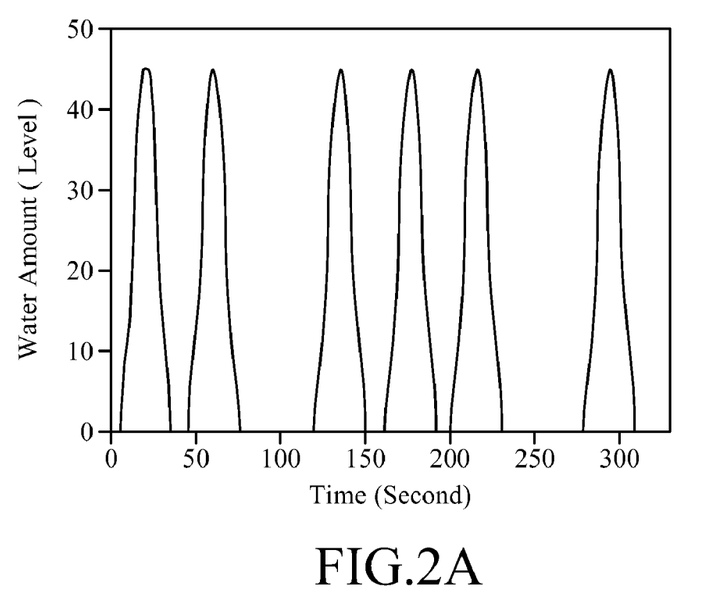
FIGS. 2A-2F are liquid level variation curves obtained by respectively detecting liquid level variations in a first rinsing tank to a sixth rising tank according to an embodiment of the present invention.
Figure 2B:
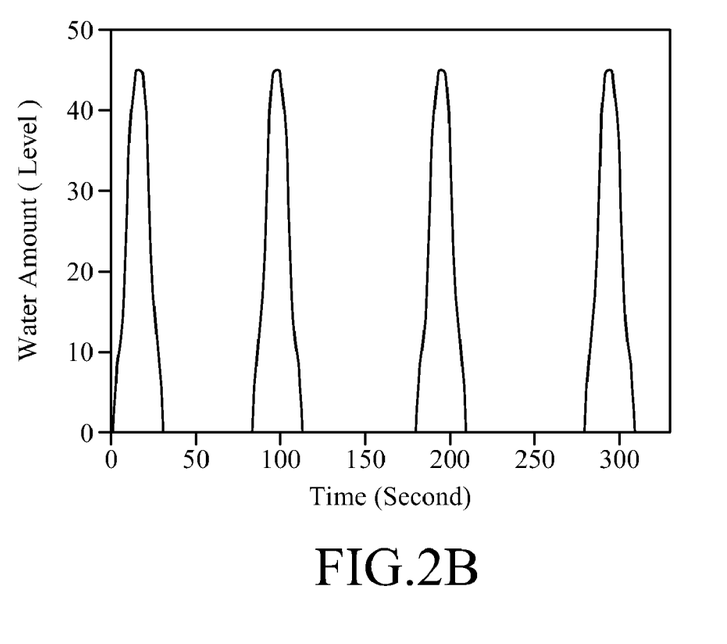
Figure 2C:
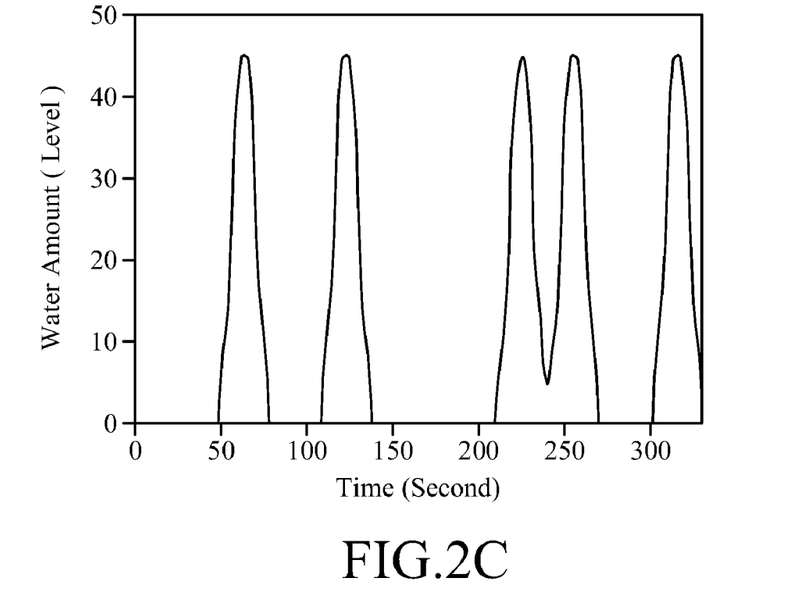
Figure 2D:
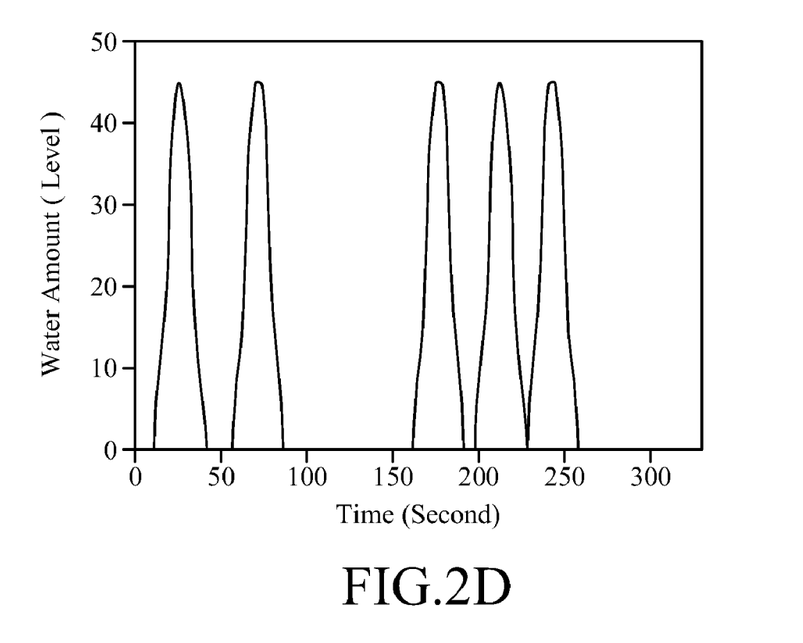
Figure 2E:
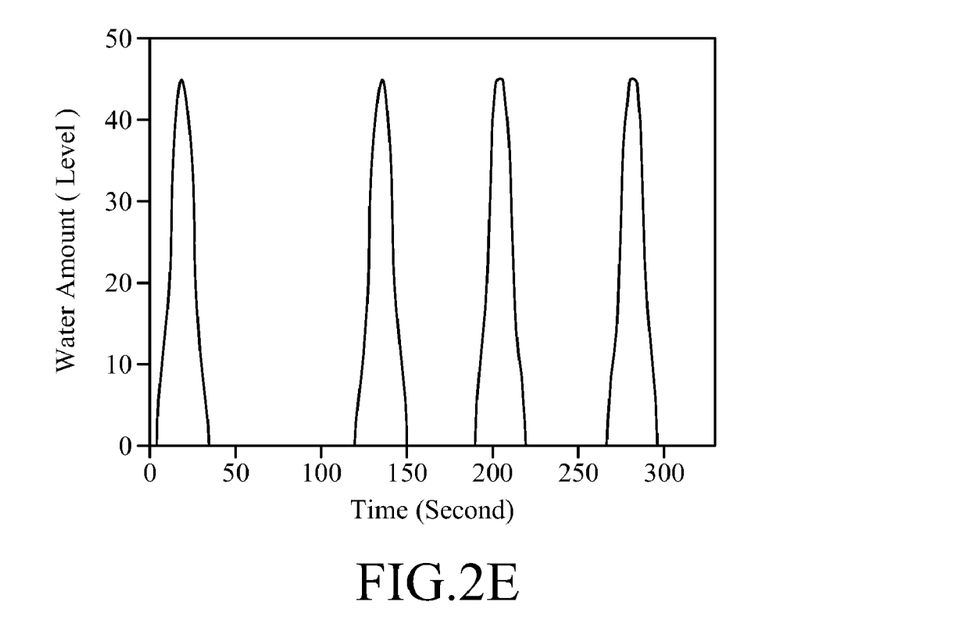
Figure 2F:
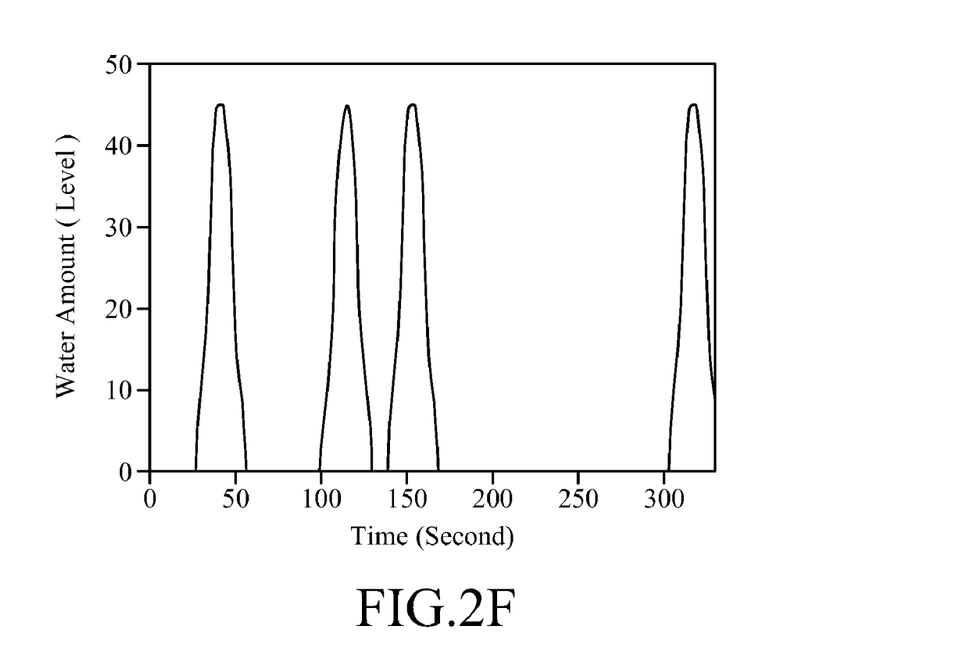
Figure 4:
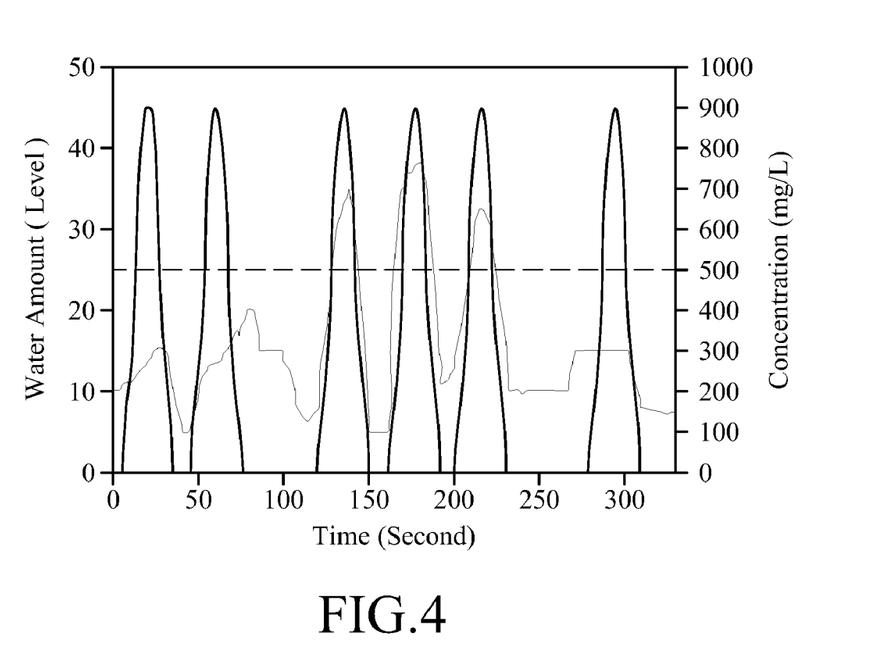
FIGS. 4-9 are fingerprint recognized figures obtained by superposing the liquid level variation curves in the first rinsing tank to the sixth rising tank and a water quality variation curve of the buffer tank in sequence according to an embodiment of the present invention.
Figure 5:
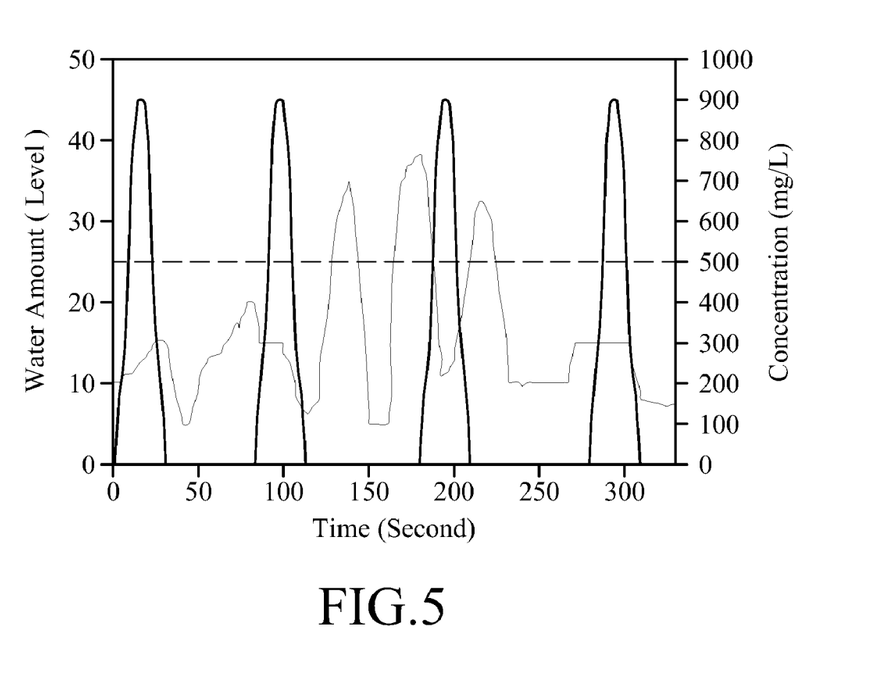
Figure 6:
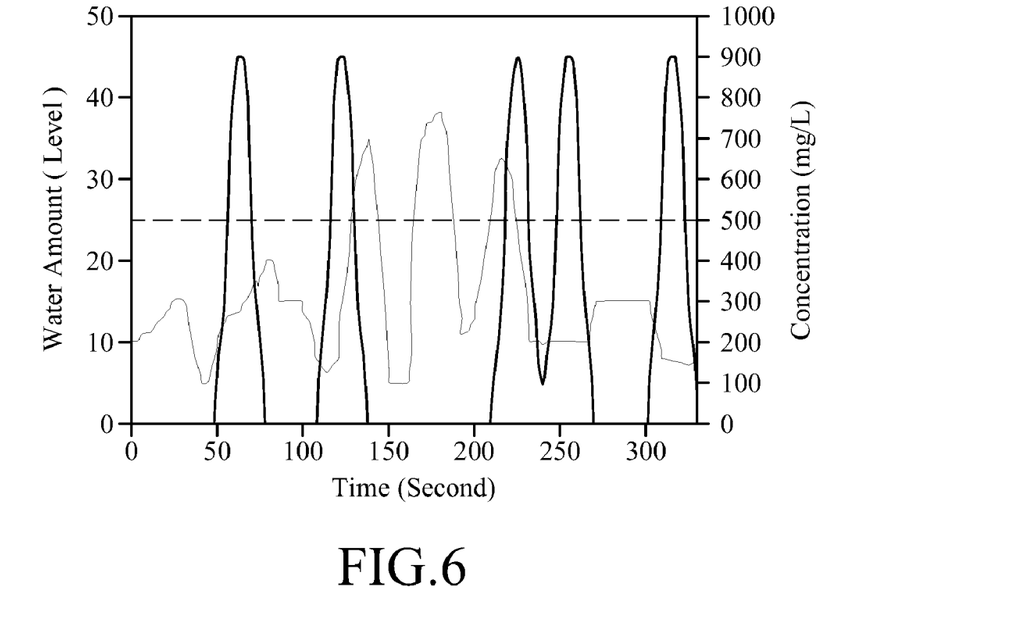
Figure 7:
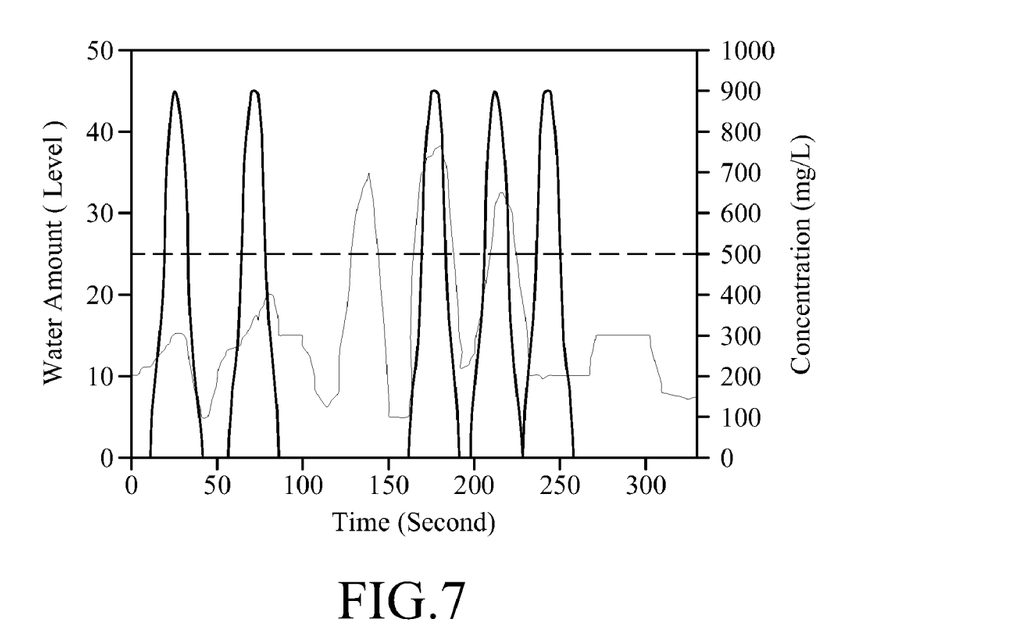
Figure 8:
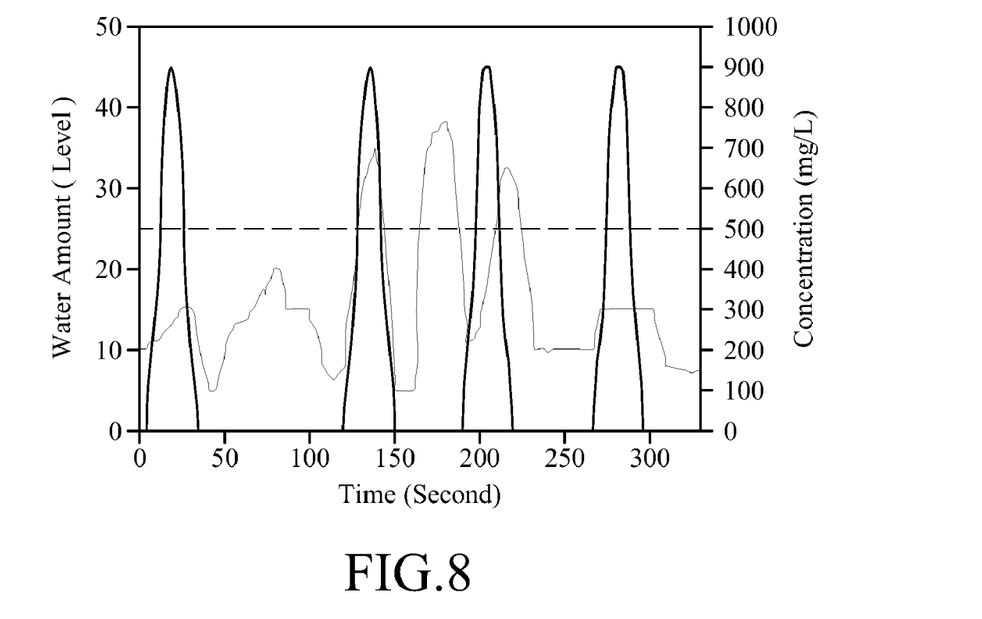
Figure 9:
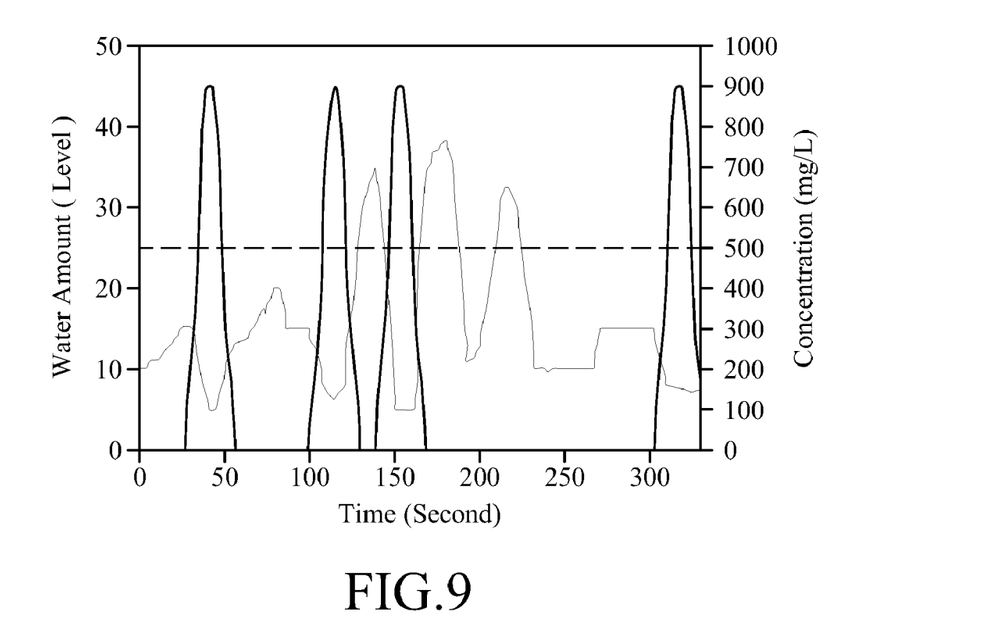

In an unknown situation, the water quality of the drain water drained from one of the rinsing tanks exceeds a predetermined water quality standard. In this embodiment, the drain water amount of a certain rinsing tank is randomly changed, and a pollutant such as sodium chloride (NaCl) is added into the rinsing tank to change the water quality concentration. Next, each liquid level variation curve and the water quality variation curve within a same time interval are respectively superposed, so as to form the fingerprint recognized figures as shown in FIGS. 4-9. Particularly, the liquid level variation curve of the first rinsing tank (as shown in FIG. 2A) and the water quality variation curve of the buffer tank (as shown in FIG. 3B) are superposed, so as to form the fingerprint recognized figure as shown in FIG. 4. Similarly, the liquid level variation curve of the second rinsing tank (as shown in FIG. 2B), the liquid level variation curve of the third rinsing tank (as shown in FIG. 2C), the liquid level variation curve of the fourth rinsing tank (as shown in FIG. 2D), the liquid level variation curve of the fifth rinsing tank (as shown in FIG. 2E), and the liquid level variation curve of the sixth rinsing tank (as shown in FIG. 2F) are respectively superposed with the water quality variation curve of the buffer tank (as shown in FIG. 3B), so as to respectively form the fingerprint recognized figures as FIGS. 5-9. In FIGS. 4-9, a thicker curve represents the liquid level variation curve of the rinsing tank, and a thinner curve represents the water quality variation curve of the buffer tank.

Next, the superposed figures are respectively compared. Firstly, referring to FIG. 4, in the range exceeding the predetermined water quality standard, peak overlap times of the water quality variation curve and the liquid level variation curve are calculated. After the calculation, it is obtained that the peak overlap times in the range exceeding the predetermined standard value of 500 mg/L in FIG. 4 are 3. Similarly, the peak overlap times in the range exceeding the predetermined standard value of 500 mg/L in FIGS. 5-9 are calculated in sequence, and are respectively 0, 0, 2, 1, and 0. Afterwards, a peak overlap ratio is further calculated according to the peak overlap times. Then, a value of possibility that each rinsing tank has the pollution source is calculated according to the obtained peak overlap ratio of each flow of drain water, so as to determine a rinsing tank having a possible pollution source.

Table 1 shows peak overlap times and values of possibility of the presence of the pollution source calculated after the liquid level variation curves of the first to the sixth rinsing tanks and the water quality variation curve of the buffer tank are respectively superposed according to an embodiment of the present invention. As shown in Table 1, in this embodiment, the possibility that the first rinsing tank has the pollution source is the highest.

TABLE 1

Peak Overlap Times and Possibility of the Presence of Pollution Source Obtained After Superposition

|  | Peak Overlap Times | Possibility of the Presence of Pollution Source (%) |
| --- | --- | --- |
| First Rinsing Tank | 3 | 99 |
| Second Rinsing Tank | 0 | 0 |
| Third Rinsing Tank | 0 | 0 |
| Fourth Rinsing Tank | 2 | 66 |

TABLE 1-continued

Peak Overlap Times and Possibility of the Presence of Pollution Source Obtained After Superposition

|  | Peak Overlap Times | Possibility of the Presence of Pollution Source (%) |
| --- | --- | --- |
| Fifth Rinsing Tank | 1 | 33 |
| Sixth Rinsing Tank | 0 | 0 |

It can be seen from the data of Table 1 that, in this embodiment, the possibility that the first rinsing tank has the pollution source is the highest, so that it can be determined that the first rinsing tank is the most suspicious pollution source. Therefore, after the rinsing tank most possibly having the pollution source is found out, an operator at the front end of the process is notified in real-time to adjust and improve the process for discharging the drain water, for example, to control an electric valve for adjusting a flow direction of the drain water. That is to say, in this embodiment, for example, the flow of drain water of the first rinsing tank is immediately guided to a waste water tank, and the flows of drain water of the second to the sixth rinsing tanks are guided to a reclaiming tank, and can be reused as ultra-pure water after simple water treatment.

Therefore, through the method of the present invention, the drain water that exceeds the predetermined water quality standard can be tracked in real-time, thereby quickly improving the process for discharging the drain water. In this manner, the water quality of the drain water in the buffer tank can be quickly stabilized, such that the flows of drain water are drained to the reclaiming system, that is, back to the ultra-pure water front end, and can be reused as ultra-pure water after simple water treatment. It can be seen that, through the method of the present invention, which rinsing tank the pollution source comes from can be quickly and accurately found out without monitoring the water quality of the drain water of every tank and changing the existing pipelines and devices of the process, thereby improving the process for discharging the drain water. Thus, the process cost and the labor force can further be greatly reduced.

What is claimed is:

1. A method for reclaiming process water, comprising:
    draining a plurality of flows of drain water from a plurality of rinsing tanks to a buffer tank, wherein a water quality of at least one of the flows of drain water exceeds a predetermined water quality standard;
    recording liquid level variations of the rinsing tanks, and respectively drawing a plurality of liquid level variation curves;
    detecting a water quality concentration in the buffer tank, and drawing a water quality variation curve;
    respectively superposing each liquid level variation curve and the water quality variation curve within a same time interval;
    respectively calculating a peak overlap ratio of the water quality variation curve and the liquid level variation curve after each superposition in a range exceeding the predetermined water quality standard;
    determining the rinsing tank having a possible pollution source according to the peak overlap ratio of each flow of drain water;
    guiding the flow of drain water of the rinsing tank having the possible pollution source to a waste water tank; and
    guiding the flows of drain water of other rinsing tanks to a reclaiming tank.

2. The method for reclaiming the process water according to claim 1, wherein before the step of respectively superposing each liquid level variation curve and the water quality variation curve within the same time interval, the method further comprises: selectively correcting the liquid level variation curves and the water quality variation curve based on a delay time of each flow of drain water.

3. The method for reclaiming the process water according to claim 2, wherein the step of selectively correcting the liquid level variation curves and the water quality variation curve based on the delay time of each flow of drain water comprises correcting the drain water amount variation curves and the water quality variation curve through a plurality of delay factors and according to a predetermined correction method.

4. The method for reclaiming the process water according to claim 3, wherein the delay factors are selected from any combination of pipe length, pipe area, pipe curvature, pipe inclination, flow time, flow rate, and flow capacity.

5. The method for reclaiming the process water according to claim 1, wherein the drain water amount variations of the flows of drain water are detected by a water amount detector.

6. The method for reclaiming the process water according to claim 1, wherein the drain water amount variations of the flows of drain water are data provided by a console.

7. The method for reclaiming the process water according to claim 6, wherein the data provided by the console is electronic signal outputs of a pneumatic valve or electronic signal outputs of an electric valve.

8. The method for reclaiming the process water according to claim 1, wherein the water quality comprises conductivity.

* * * * *

UNITED STATES PATENT AND TRADEMARK OFFICE
CERTIFICATE OF CORRECTION

| | | |
|---|---|---|
| PATENT NO. | : 8,196,596 B2 | Page 1 of 1 |
| APPLICATION NO. | : 13/315112 | |
| DATED | : June 12, 2012 | |
| INVENTOR(S) | : Chien-Hung Chen et al. | |

It is certified that error appears in the above-identified patent and that said Letters Patent is hereby corrected as shown below:

On the Title page:

Item (75) Inventors:

Please delete the name of the inventor "~~Meng Chun Huang~~".

Please add the name of the inventor -- Meng-Shun Huang --.

Signed and Sealed this
Fourth Day of September, 2012

David J. Kappos
*Director of the United States Patent and Trademark Office*